United States Patent [19]

Arathoon et al.

[11] Patent Number: 5,053,334
[45] Date of Patent: Oct. 1, 1991

[54] PROCESS FOR PRODUCING BIOLOGICALLY ACTIVE PLASMINOGEN ACTIVATOR IN RECOMBINANT CHO CELLS USING SUSPENSION CULTURE AND REMOVING DETRIMENTAL COMPONENTS FROM MEDIUM

[75] Inventors: William R. Arathoon, San Francisco; Stuart E. Builder, Belmont; Anthony S. Lubiniecki, San Ramon; Robert D. van Reis, Redwood City, all of Calif.

[73] Assignee: Genentech, Inc., South San Francisco, Calif.

[21] Appl. No.: 522,073

[22] Filed: May 9, 1990

[51] Int. Cl.$^5$ ............................................. C12N 9/64
[52] U.S. Cl. .................................................. 435/226
[58] Field of Search ..................... 435/212, 226, 240.2, 435/240.241, 240.242, 240.25; 935/61, 70

[56] References Cited

U.S. PATENT DOCUMENTS

| | | | |
|---|---|---|---|
| 3,904,480 | 9/1975 | Hull et al. | 435/217 |
| 4,232,124 | 11/1980 | Mann | 435/212 |
| 4,317,882 | 3/1982 | Horiguchi et al. | 435/212 |
| 4,328,314 | 5/1982 | Horiguchi et al. | 435/212 |
| 4,391,912 | 7/1983 | Yoshida et al. | 435/240.25 |
| 4,409,331 | 10/1983 | Lim | 435/178 |
| 4,420,398 | 12/1983 | Castino | 435/240.241 |
| 4,505,893 | 3/1985 | Mori et al. | 424/94.64 |
| 4,537,860 | 8/1985 | Tolbert et al. | 435/240.242 |
| 4,546,083 | 10/1985 | Meyers et al. | 435/240.25 |
| 4,740,461 | 4/1988 | Kaufman | 935/32 X |
| 4,757,005 | 7/1988 | Chan | 435/69.1 |

FOREIGN PATENT DOCUMENTS

| | | |
|---|---|---|
| 0093619 | 9/1983 | European Pat. Off. . |
| 0113319 | 11/1984 | European Pat. Off. . |
| 0158958 | 10/1985 | European Pat. Off. ............ 435/226 |
| 211260 | 2/1987 | European Pat. Off. . |
| 0219791 | 4/1987 | European Pat. Off. . |
| 248675 | 12/1987 | European Pat. Off. ......... 435/172.3 |
| WO85/03011 | 7/1985 | PCT Int'l Appl. . |
| WO86/05514 | 9/1986 | PCT Int'l Appl. .............. 435/172.3 |
| WO87/01389 | 3/1987 | PCT Int'l Appl. ................ 435/212 |

OTHER PUBLICATIONS

Kruithof, E. K. O. et al., (1985) *Biochem. J.*, 226: 631.
Rijken, et al., *J. Biol. Chem.*, vol. 256, pp. 7035–7041, 1981.
Kaufman et al., *Molec. & Cell. Biol.*, vol. 5, pp. 1750–1759, Jul. 1985.
Brouty-Boye et al., "Biosynthesis of Human Tissue-Type Plasminogen Activator by Normal Cells", *Bio/Technology*, p. 1058 (Dec. 1984).
The Large-Scale Cultivation of Mammalian Cells, *Scien. Am.*, 248, vol. 1, 36–43 (Jan. 1983).
Large-Cell Culture in Biotechnology, *Science*, 232, 1390–1395 (Jun. 1986).

*Primary Examiner*—Richard A. Schwartz
*Assistant Examiner*—Marianne Porta
*Attorney, Agent, or Firm*—Walter H. Dreger

[57] ABSTRACT

A method of producing biologically active human tissue plasminogen activator in suspension culture is provided wherein recombinant Chinese hamster ovary cells are cultured and certain components detrimental to recovery and biological activity are removed as a cell-free filtrate by cross-flow filtration. The human tissue plasminogen activator is recovered from the culture medium.

8 Claims, 1 Drawing Sheet

1 2 3 4 5 6 7 8 9 10 11 12 13 14 15

1 2 3 4 5 6 7 8 9 10 11 12 13 14 15

PROCESS FOR PRODUCING BIOLOGICALLY ACTIVE PLASMINOGEN ACTIVATOR IN RECOMBINANT CHO CELLS USING SUSPENSION CULTURE AND REMOVING DETRIMENTAL COMPONENTS FROM MEDIUM

This application is a continuation of application Ser. No. 06/871,642, filed Jun. 6, 1986, now abandoned.

FIELD OF THE INVENTION

The present invention is directed to processes for producing biologically active human tissue-type plasminogen activator and derivatives, particularly from recombinant suspension host cell cultures.

BACKGROUND OF THE INVENTION

Human tissue-type plasminogen activator converts plasminogen to plasmin. The plasmin, so produced, proteolytically cleaves fibrin matrices which comprise the backbone of blood clots. Human tissue-type plasminogen activator thereby mediates the dissolution of blood clots and is consequently useful in the treatment of various thrombotic disorders.

The abbreviation "t-PA" for human tissue-type plasminogen activator was adopted after proposal at the XXVIII Meeting of the International Committee on Thrombosis and Hemostatis, Bergamo, Italy, July 27, 1982. As used herein, the terms "human tissue-type plasminogen activator", "human t-PA", "t-PA", "human tissue plasminogen activator" or "tissue plasminogen activator" denote human extrinsic (tissue-type) plasminogen activator, produced, for example, from natural source extraction and purification [see Collen et al., European Patent Application No. 41766 (published Dec. 16, 1981 based upon a first filing of June 11, 1980) and Rijken et al., *Journal of Biol. Chem.* 256, 7035 (1981), incorporated herein by reference], and by recombinant cell culture systems as described together with the amino acid sequence and other characteristics of the molecule, for example, in European Patent Application Publication No. 93619, (published Nov. 9, 1983 based upon a first filing of May 5, 1982), incorporated herein by reference. The terms also cover biologically active human tissue-type plasminogen activator equivalents, differing in glycosylation patterns, which are thought to be dependent on the specific culture conditions used and the nature of the host from which the human tissue-type plasminogen activator is obtained, and differing in one or more amino acid(s) in the overall sequence.

Researchers in Assignee's laboratories produced human tissue-type plasminogen activator, essentially free of proteins with which it is ordinarily associated, via recombinant DNA technology in prokaryotic and eukaryotic hosts. (See EPA 93619, supra.) Several reasons attend the preferable production of human tissue-type plasminogen activator in recombinant eukaryotic hosts, such as mammalian cells. Eukaryotic hosts in general are efficient in their ability to recognize and glycosylate specific amino acid residues in the human tissue-type plasminogen activator molecule which are ordinarily glycosylated in the native state, generate the naturally occurring covalent cross-linkages between various cysteine residues of the human tissue-type plasminogen activator molecule, and more closely approximate the overall conformational structure of native human tissue-type plasminogen activator. These features are thought to be important for producing a biologically active and safe human tissue-type plasminogen activator product.

However, the production of human tissue-type plasminogen activator from recombinant host cells is not without attendant problems. Thus, it has been found that yield-limiting difficulties arise because the cells producing human tissue-type plasminogen activator are customarily cultured in the presence of serum, various fractions derived from blood or other animal tissues or hydrolysates thereof. As a consequence, the human tissue-type plasminogen activator secreted by such cells is exposed to large amounts of serum proteins and other serum components. It was found that certain of these components invariably complicate the purification of an intact human tissue-type plasminogen activator to a pharmaceutically acceptable form because they form difficult-to-separate bound aggregate complexes with the human tissue-type plasminogen activator molecule. These aggregates also interfere with the biological activity of the human tissue-type plasminogen activator molecule, thus reducing overall the ordinarily expected yields of biologically active intact human tissue-type plasminogen activator. Addition of serum components also increases the mass of impurities that must be removed during purification. Further, many of these components proteolytically degrade tissue-type plasminogen activator. Purification of the desired human tissue-type plasminogen activator from these systems pose technical difficulties, consequently requiring more expensive procedures.

Consistent with these observations, serum-free media have been suggested in attempts to avoid problems in producing and purifying endogenously produced plasminogen activators secreted by cultured cells. See, for example, 1) European Patent Application Publication No. 113319 (published July 11, 1984, based upon a first filing of December 30, 1982) which discloses the preparation of serum-independent natural human cell lines secreting endogenously-produced human tissue-type plasminogen activator, 2) U.S. Pat. No. 4,232,124, 3) U.S. Pat. No. 4,328,314, 4) U.S. Pat. No. 4,317,882, and 5) Gasser et al., *In Vitro Cellular and Developemental Biology* 21, 588 (1985). None of these references relate to high density cell growth, and in particular to recombinant suspension host cell cultures. On the other hand, European Patent Application Publication No. 112940 (published July 11, 1984, based upon a first filing of Dec. 30, 1982) is directed to a process of producing human tissue-type plasminogen activator involving the addition of albumin, a protein component of serum.

Various means for fractionating cell cultures to remove, for example, serum components are also known. See, for example, Van Reis et al., *The Journal of Immunology* 133, 758 (1984) who reduced plasma protein levels from leukocyte cell cultures thereby reducing impurities of crude endogenously produced human gamma interferon. (See also Van Reis et al., *Methods in Enzymology* 119, 77). In November, 1982, at the Third Annual International Congress for Interferon Research in Miami, Florida, Van Reis et al., reported on the use of cross-flow filtration to reduce levels of autologous plasma protein in recovering endogenously-produced human gamma interferon from a human cell culture. However, the amount of interferon recovered could not be increased with further removal during production.

It is an object of the present invention to provide processes for the (large-scale) production and recovery of biologically active human tissue-type plasminogen activator from a culture of human tissue-type plasminogen activator producing host cells. It is a further object of the present invention to provide such processes for production of biologically active human tissue-type plasminogen activator which is substantially free from proteolytic degradation, deglycosylation, inhibition by various protease inhibitors, and contamination and aggregation with serum components.

SUMMARY OF THE INVENTION t-PA producing host cells, such as those that have been transfected with recombinant vectors operably harboring DNA encoding human tissue-type plasminogen activator, is grown in a growth supporting medium preferably containing one or more components that while facilitating cell growth, are detrimental to the recovery and activity of the expressed human tissue-type plasminogen activator product. Substantially all of such components are excluded prior to culturing or removed from the growth support medium by medium exchange, preferably via cross-flow filtration, during the culturing. After removal, the host cell culture retains expression ability with or without necessity of further cell replication.

Biologically active human tissue-type plasminogen activator is thereafter produced by expression in the cells maintained in the host cell culture substantially free from detrimental components. The biologically active human tissue-type plasminogen activator is then isolated from the cells prior to further purification fitting it for pharmaceutical administration.

Unexpectedly, the process of the present invention enables production of purified, intact human tissue-type plasminogen activator in yields not hitherto thought achievable. Further, the processes of the present invention provides biologically active human tissue-type plasminogen activator having a composition of at least 50 percent single-chain form versus product having a composition of substantially less single-chain form obtained prior to the present processes. This is thought to be significant, in addition to being unexpected, because it indicates that the processes hereof produce product substantially free of proteolytic degradation at various cleavage sites. Further, material which is predominantly in single-chain form appears to have at least the same efficacy as two-chain material and exhibits less fibrinogen breakdown, results which may have significance in clinical applications.

DETAILED DESCRIPTION

A. General

In the case of mammalian host cell cultures, the detrimental medium components typically are blood or other animal tissue derived proteases, glycosidases such as neuramididase, protease inhibitors, albumin, etc. which are initially present in the growth supporting medium.

The term "biologically active human tissue-type plasminogen activator" refers to the above-described human tissue-type plasminogen activator which is capable of mediating the in vivo dissolution of fibrin blood clots.

The term "host cell culture" refers to a culture of t-PA producing host cells, such as those that have been transfected with an expression vector operably harboring DNA encoding tissue-type plasminogen activator. "Recombinant host cell culture" is a "host cell culture" tranfected with an expression vector operably harboring DNA encoding tissue-type plasminogen activator. "Recombinant suspension host cell culture" systems are preferred.

A wide variety of host cells may be employed herein. Suitable host cells preferably are capable of being transfected with recombinant vectors operably harboring human tissue-type plasminogen activator encoding DNA, producing by expression biologically active human tissue-type plasminogen activator and being susceptible to growth and maintenance in suspension culture. Accordingly, any host cell that produces t-PA and/or is amenable to recombinant engineering to produce recombinant human tissue-type plasminogen activator is within the scope of the invention. Host cells are preferably mammalian and include recombinant human tissue-type plasminogen activator secreting Chinese hamster overy (CHO) cells (see EPA 93619, supra.) (ATCC No. CCL61).

In the process of the present invention, host cells capable of producing human tissue-type plasminogen activator are first grown as a growth suspension in a "growth supporting medium". This growth supporting medium may be any standard medium known in the art, or variations thereof, to support a culture of the particular cell line used to produce human tissue-type plasminogen activator. [See, for example, *ATCC Media Handbook*, Ed: Cote et al., American Type Culture Collection, Rockville, MD (1984).] A growth supporting medium for mammalian cells, for example, preferably contains a serum supplement such as fetal calf serum or other supplementing component commonly used to facilitate cell growth and division such as hydrolysates of animal meat or milk, tissue or organ extracts, macerated clots or their extracts, and so forth. The initial growth supporting medium may also be a medium which permits the growth and maintenance of the host cells and the expression of human tissue-type plasminogen activator. In addition, a standard growth medium deficient in glycine and/or hypoxanthine and/or thymidine and/or containing methotrexate may be used to maintain selective pressure for recombinant CHO cells containing an expression vector capable of expressing human tissue-type plasminogen activator, as well as dihydrofolate reductase having a low binding affinity for methotrexate. Other selectable and/or amplifiable markers may also be employed. Other suitable medium components include, for example, transferrin, insulin and various metals.

In one embodiment, after the host cells have grown to an appropriate cell density, e.g., about $1 \times 10^6$/ml to $3 \times 10^7$/ml for CHO cells, the detrimental components in the growth supporting media are removed by medium exchange, preferably via "cross-flow filtration". Cross-flow filtration refers to a mode of filtration where a suspension of human tissue-type plasminogen activator producing cells flows substantially parallel to a filter which is permeable to a component of the suspension other than cells.

The cross-flow filtration process is characterized by a set of fluid dynamic parameters including Re=Reynolds number, $\gamma_w$=wall shear rate, $\Delta P$=pressure drop and TMP=transmembrane pressure. Re, $\gamma_w$ and $\Delta P$ will depend on the geometry of the filtration system, flow conditions and fluid properties. For example, if a hollow fiber filtration system is employed, one may calculate these parameters as follows:

$$Re = 2\rho Q_s/\eta_s n\pi r_h$$

$$\gamma_w = 4Q_s/n\pi r_h^3$$

$$\Delta P = 8Q_s L\eta_s/n\pi r_h^4$$

where $\rho$ = the cell suspension density, $Q_s$ = suspension recirculation flow rate, $\eta_s$ = suspension dynamic viscosity, n = number of hollow fibers, $r_h$ = hollow fiber inner radius and L = hollow fiber length. Similiar equations may be derived for other flow path geometries. The average transmembrane pressure can be calculated as:

$$TMP = P_{in} - P_f - \Delta P/2 = Q_f R \eta_f / A$$

where $P_{in}$ = inlet pressure, $P_f$ = filtrate pressure, $Q_f$ = filtration rate, R = membrane resistance, A = membrane area and $\eta_f$ = filtrate dynamic viscosity. In a preferred embodiment the flow path geometry and operating parameters are chosen so as to minimize cell deposition onto the filtration membrane, thereby enhancing the efficiency of the separation process and minimizing shear induced cellular damage. Cell deposition may be empirically determined as:

$$DP = \nu^{\frac{1}{2}} U \lambda / r_c^2 \gamma^{3/2}$$

where DP = deposition parameter, $\nu$ = kinematic viscosity, U = filtration velocity, $\lambda$ = empirical function of cell concentration, $C_c$ and $r_c$ = cell radius. Hence, the cross-flow filtration process will be defined by the cell suspension ($\rho$, $\eta_s$, $\eta_f$, $\nu$, $C_c$ amd $r_c$), selection of membrane and flow geometry (n, $r_h$, L, R and A) and by control of operating parameters ($Q_s$ and $Q_f$). In a preferred embodiment, the flow path geometry and operating conditions are chosen such that Re < 2100 and DP < 0.35.

The concentration of detrimental components is reduced by a cross-flow filtration process in which the cell suspension is recirculated through the filtration apparatus and a portion of the flow is taken off as a cell-free filtrate. A constant cell suspension volume may be maintained by adding media which does not contain detrimental components. The final residual proportion of detrimental components can be calculated as:

$$C_p = \frac{C_o V_x e^{(-V_m/V_x)}}{V_p}$$

where $C_p$ = concentration of detrimental components in the production suspension, $C_o$ = initial concentration of detrimental components in the cell growth suspension, $V_x$ = volume of cell suspension during medium exchange, e = natural log base, $V_m$ = volume of exchange media and $V_p$ = final volume of production suspension. The volume of exchange media required to reduce the concentration of detrimental components to a predetermined level may be calculated as:

$$V_m = V_x \ln(C_o V_x / C_p V_p)$$

where ln = natural log. It is evident from this equation that a preferred embodiment of this invention would involve an initial concentration of the cell suspension to a minimal value $V_x$ prior to the aforementioned constant volume media exchange. Reduction of the concentration of detrimental components is thus accomplished by I) concentrating the cell growth suspension from its initial volume $V_o$ to $V_x$; II) performing a constant volume media exchange and III) further reduction if $V_x < V_p$.

Thus, for example, if the volume of the initial cell culture prior to medium exchange is 100 liters, an overall 10,000-fold reduction in concentration of detrimental components can be achieved by concentrating the cell suspension to 10 liters, performing a media exchange using 45 liters of media and using a production volume of 1,000 liters.

It is thus possible to determine quantitatively the dilution factor of the initial growth support medium during medium exchange such that the amount of the detrimental components in the resulting host cell suspension are below a predetermined concentration thereby minimizing the adverse effects of such components. Such dilution factors may be determined for each batch of growth medium. For example, mammalian growth media supplemented with different concentrations of serum may require different dilution factors to reduce the amount of undesirable components to functionally equivalent concentrations which permit the production of pharmaceutically acceptable human tissue-type plasminogen activator. Accordingly, the dilution factor may be chosen such that the amount of serum in the final mammalian expression medium is, for example, less than about 1 percent of the total initially employed.

The filtration membranes used herein may be selected from any of those known in the art having a suitable membrane and configuration, such that they are capable of retaining the human tissue-type plasminogen activator producing cells of the present invention whilst allowing the various detrimental components to pass therethrough. Thus, one may employ any suitable membrane which permits the retention of cells under the fluid dynamic conditions selected whilst allowing the detrimental components to pass through for removal. An upper limit of pore size of about 5 microns and a lower limit of about 0.1 microns would be suitable.

The fresh exchange medium is substantially free of the detrimental components. For example, it does not contain any significant amounts of detrimental components, e.g. proteases, neuraminidases, protease inhibitors, etc. Such medium, of course, will vary with the cell type used to produce human tissue-type plasminogen activator, and can be selected from those available in the art, for example. It may be the same as the final, expression medium (for convenience), or some less rich medium such as a buffered, isotonic saline medium.

For the human tissue-type plasminogen activator producing CHO cells described herein, for example, final, expression medium may be formed from a standard medium for culturing CHO cells which is not supplemented with fetal calf serum. An example of the final, expression medium is an equal-parts mixture of Dulbecco-modified Eagles medium (high glucose) and Ham's F-12 medium.

In other embodiments, the detrimental components may be excluded, or substantially excluded, from the medium prior to culturing or they may be removed by centrifugation or settling techniques, for example.

The human tissue-type plasminogen activator is isolated and is thereafter purified from the expression medium and used as a pharmaceutical agent for the treatment of various vascular conditions or diseases.

B. Preferred Embodiment

In a preferred embodiment, CHO cells capable of producing human tissue-type plasminogen activator are grown as a suspension in a CHO medium supplemented with fetal calf serum to a predetermined cell density. The cell suspension is then concentrated by cross-flow filtration. Serum is thereafter removed from the concentrated suspension by constant volume cross-flow filtration while continuously adding serum free medium at the same rate as serum containing medium is removed. Active human tissue-type plasminogen activator is produced subsequently by the CHO cells suspended in the serum-free expression medium. The human tissue-type plasminogen activator thus produced is secreted by the CHO cells into the expression medium and may be separated from it by standard techniques.

Culture vessels of various capacities are used to grow suspensions of CHO cells. Each culture vessel is connected via inlets to an array of porous tangential flow filters which in turn are connected via outlets back to the culture chamber. After growth, the suspensions of CHO cells and medium containing serum are pumped through the array of porous tangential flow filters firstly to concentrate the suspension and thereafter to allow removal of the serum components from the suspension during medium exchange. The CHO cell suspension is recycled through the filters and culture vessel allowing a portion of the old medium and serum components to be removed. A supply of fresh sterile expression medium which does not contain serum is added to the cell suspension to maintain a nominal volume in the culture vessel. After the serum concentration has been reduced in this way to a predetermined concentration by continuous medium exchange, the cells are transferred via sterilized tubes to another vessel containing serum free expression medium into which human tissue-type plasminogen activator is secreted. Thereafter, the human tissue-type plasminogen activator may be removed by standard techniques.

C. Examples

Cell Growth, Medium Exchange and Production Phases.

Chinese Hamster Ovary (CHO) cells (ATCC No. CCL61), transfected with the expression vector pETPFR (See EPO 93619 supra.) and therefore expressing recombinant t-PA, were revived from storage over liquid nitrogen and grown in medium consisting of a 1:1 mixture of Hams F12 and Dulbecco Modified Eagle medium. This mixture did not contain hypoxanthine or thymidine. Dialyzed or diafiltered fetal bovine serum (7% v/v) and methotrexate (to 500 nM) were added to the medium. The cells were grown in suspension culture in glass vessels incubated at about 37° C. Cells were subcultivated and the population expanded in this medium every three to five days. When sufficient cells had accumulated they were transferred into a 10 L stainless steel fermenter for a further growth period of about three days. For this growth phase the medium composition was changed to give better cell yields and contained both hypoxanthine and thymidine but no methotroxate. In this medium undialysed fetal bovine serum was incorporated (2% v/v) and during the three day growth phase the cell population density increased from about $0.25 \times 10^6$ cells/mL to about $1.0 \times 10^6$ cells/mL.

The cells were then subjected to medium exchange as described before being resuspended in serum-free production medium for about 90 hours. The medium exchange was effected as follows:

A hollow fiber tangential flow filter and associated inlet and outlet silicone rubber tubing was sterilized in an autoclave and then connected to the 10 L production vessel via steam sterilizable connections. The filter used was a polysulfone hollow fiber unit (Manufacturer: A.G. Technology, Inc., filter #1BZE100801AL) containing 280 hollow fibers with 0.75 mm internal diameters and nominally 0.1 μm pores along their lengths. This unit had a filtration area of 4.15 ft.$^2$. The cells were recirculated through the hollow fibers and back to the vessel by use of a Watson Marlow two lobed pump. A recirculation rate of appproximately 3.5 liters per minute was used and at the same time a portion of the fluid was drawn off and discarded as a clear filtrate at a rate of about 211 mLs per minute. In this way, the cells were retained and the culture volume reduced to approximately 5.2 liters. At this time fresh sterile serum-free medium (of the same formulation used previously but containing no bovine serum or components derived from it) was pumped into the culture vessel at a rate of about 211 mLs per minute thus maintaining the volume while constantly diluting out the old medium.

55 liters of fresh serum free medium were pumped through the system to give a calculated reduction in serum concentration of about 190,000 fold (or less than 0.0001% by volume) when an aliquot of the cell suspension was added to fresh serum free medium in a separate 10 L stainless steel fermenter. The cells were then incubated for the production phase for about 90 hours at 37° C. Samples were removed from the culture, clarified by centrifugation and stored at −20°20° C. for subsequent analysis.

In a second example, which was run in parallel, all the conditions, cells and media used were similar except the hollow fiber filter. In this case, the filter contained 290 hollow fibers and had a filtration area of 4.3 ft.$^2$ but was otherwise similar to the one described above (Manufaturer: A.G. Technology, Inc., filter #1810902 AL).

Methods of Analysis

Samples were treated and analyzed to demonstrate the detrimental effects of bovine serum on t-PA produced by the CHO cells used in these examples. Samples of the clarified cell culture fluid from the serum-free production phase were thawed, reduced with β mercaptoethanol and subjected to S.D.S. electrophoresis using the Laemmli discontinuous system (Laemmli, *Nature*, 227, 680, (1970)). The proteins separated in this way were subjected to silver straining (Morrissey, *Anal. Biochem.* 117, 307, (1981)) or were transferred to a nitrocellulose sheet, (transfer for 4 hours at 8° C. and 0.5 amps onto 0.45 μm nitocellulose using the method of: Towbin, et al., PNAS 76, 6350, (1979)). The t-PA proteins, protein fragments and high molecular weight complexes containing t-PA were visualised on the nitrocellulose sheet by an indirect enzyme linked immunoassay technique described as follows: An initial reaction with the bound t-PA proteins and rabbit anti-t-PA antibody was followed by treatment with a second antibody. This was a horseradish peroxidase linked anti-rabbit IgG (raised in goats). After this reaction, addition of the chromophore 4-Cl-napthol in $H_2O_2$ and PBS resulted in cc·or development in the regions of bound antibody thereby illustrating the electrophoretic patterns of t-PA and associated proteins. Thus, using these techniques the state of the t-PA in the crude culture fluids could be determined without further purification.

Results

To demonstrate the detrimental effects of fetal bovine serum on t-PA, samples from the production phase were incubated with phosphate buffered saline (PBS) or with 0.175% v/v or 1.75% v/v fetal bovine serum for 22 hours or 46 hours prior to being analysed as described above. Results of this are shown in the silver stained gel of FIG. 1 and the corresponding immunoblot in FIG. 2.

DESCRIPTION AND ANALYSIS OF THE FIGURES

| Lane No. | Sample |
|---|---|
| 1 | Molecular weight standards [92.5 Kilodaltons (KD), 66.2KD, 45KD, 31KD, 21.5KD, 14.4KD] |
| 2 | Authentic t-PA reference standards |
| 3 | Cell culture fluid containing t-PA (Laboratory reference) |
| 4 | Cell culture fluid from production phase sample |
| 5 | Production phase sample; Incubated 22h at 37° C. with phosphate buffer saline (PBS) |
| 6 | Production phase sample; Incubated 46h at 37° C. with PBS |
| 7 | Blank lane |
| 8 | Production phase sample; Incubated 22h at 37° C. with 0.175 percent (v/v) fetal bovine sample (FBS) |
| 9 | Production phase sample; Incubated 46h at 37° C. with 0.175 percent (v/v) FBS |
| 10 | 0.175 percent (v/v) FBS alone; Incubated 22h at 37° C. |
| 11 | 0.175 percent (v/v) FBS alone; Incubated 46h at 37° C. |
| 12 | Production phase sample; Incubated 22h at 37° C. with 1.75 percent (v/v) FBS |
| 13 | Production phase sample; Incubated 46h at 37° C. with 1.75 percent (v/v) FBS |
| 14 | 1.75 percent (v/v) FBS alone; Incubated 22h at 37° C. |
| 15 | 1.75 percent (v/v) FBS alone; Incubated 46h at 37° C. |

Figure 1:
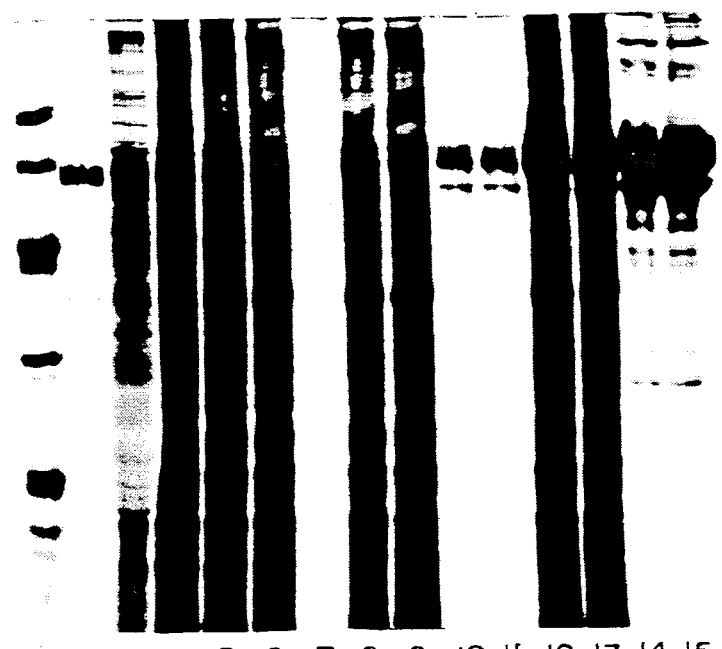
FIG. 1 is a silver stained gel of t-PA samples obtained as described above.
Figure 2:
FIG. 2 is an immunoblot of an identical gel shown in FIG. 1.

In FIGS. 1 and 2, Lanes 2 and 3 are t-PA reference standards (single chain t-PA showing as the higher molecular weight band and two chain t-PA showing as the lower molecular weight bands).

The observed detrimental effects of having fetal bovine serum (FBS) present are a) to cause a disappearance of intact t-PA with a concomitant accumulation of various proteolytically cleaved forms and fragments thereof (see Lanes 8 & 9 of FIG. 2) and b) the formation of higher molecular weight complexed material in the range of 90 to 200K daltons (see Lanes 12 & 13 of FIG. 2).

The results show that when the serum-free cell culture fluid, obtained as described above under "Cell growth, Medium Exchange and Production Phases", was incubated in the presence of PBS for 22 or 46 hours it remained substantially unchanged, (see Lanes 5 and 6, FIGS. 1 and 2). Thus, both proteolytic degradation and formation of high molecular weight complexes of t-PA result if fetal bovine serum is permitted to remain in the production phase cell culture medium. Therefore, removal of serum by the medium exchange process described herein substantially removes its detrimental effects.

Although the foregoing refers to particular preferred embodiments, it will be understood that the present invention is not so limited. It will occur to those ordinarily skilled in the art that various modifications may be made to the disclosed embodiments and that such modification are intended to be within the scope of the present invention.

We claim:

1. A method of producing biologically active tissue-type plasminogen activator in a recombinant host cell suspension culture capable of producing by recombinant expression biologically active human tissue-type plasminogen activator comprising:

a. growing recombinantly transfected Chinese hamster ovary (CHO) host cells in suspension culture using a growth supporting medium that permits the growth and maintenance of the host cells;

b. removing from the medium of said culture components in the medium that are detrimental to recovery and biological activity of said human tissue-type plasminogen activator, whilst retaining the expression capability of the host cells by a cross-flow filtration process characterized by a set of fluid-dynamic parameters utilizing a filtration apparatus having a suitable membrane such that cell culture suspension is recirculated through said filtration apparatus and a portion of the medium removed as a cell-free filtrate whilst retaining the homogeneous characteristic of said cell culture suspension;

c. replacing said filtrate with a medium devoid of components that are detrimental to recovery and activity of human tissue type plasminogen activator; and d. collecting said biologically active human tissue-type plasminogen activator expression product present in the medium exchanged culture.

2. The method according to claim 1 wherein said cross-flow filtration is performed across a flat filtration membrane.

3. The method according to claim 1 wherein said cross-flow filtration is performed across the wall of a porous hollow fiber.

4. The method according to claim 1 wherein said cross-flow filtration is performed across a spiral wound membrane.

5. The method according to claim 1 wherein said growth supporting medium components are derived from blood or tissue or derivatives thereof.

6. The method of claim 1 wherein said host cells contain an expression vector capable of expressing human tissue-type plasminogen activator and an amplifiable marker, and additionally comprising culturing said cells in a medium chosen so as to maintain selective pressure for cells containing multiple copies of said amplifiable marker prior to step (d).

7. The method of claim 6 wherein said amplifiable marker is dihydrofolate reductase having a low binding affinity for methotrexate and wherein said medium chosen so as to maintain selective pressure contains methotrexate.

8. The method of claim 1, wherein said cross flow filtration process is characterized by a cell deposition parameter, DP, and a set of fluid dynamic parameters including Re = Reynold's number, and wherein said cell suspension, said apparatus and the operating conditions of said apparatus are selected such that Re is less than 2100 and DP is less than 0.35.

* * * * *

UNITED STATES PATENT AND TRADEMARK OFFICE
CERTIFICATE OF CORRECTION

PATENT NO. : 5,053,334

DATED : 1 October 1991

INVENTOR(S) : ARATHOON, et al.

It is certified that error appears in the above-identified patent and that said Letters Patent is hereby corrected as shown below:

On the Title page, under
Related U.S. Application Data

(63) Continuation of Ser. No. 06/871,642 filed June 6, 1986, now abandoned.

Signed and Sealed this

Nineteenth Day of October, 1993

Attest:

BRUCE LEHMAN

*Attesting Officer*       *Commissioner of Patents and Trademarks*